(12) United States Patent
Castro Fresno

(10) Patent No.: US 7,455,155 B2
(45) Date of Patent: Nov. 25, 2008

(54) IMPACT ABSORBENT ASSEMBLY IN SLOPE PROTECTION SYSTEMS

(75) Inventor: Daniel Castro Fresno, Santander (ES)

(73) Assignee: Malla Talud Cantabria, S.L, Barros (ES)

( * ) Notice: Subject to any disclaimer, the term of this patent is extended or adjusted under 35 U.S.C. 154(b) by 0 days.

(21) Appl. No.: 11/651,270

(22) Filed: Jan. 9, 2007

(65) Prior Publication Data
US 2007/0125613 A1 Jun. 7, 2007

Related U.S. Application Data

(63) Continuation of application No. PCT/ES2005/000442, filed on Aug. 2, 2005.

(30) Foreign Application Priority Data

Oct. 15, 2004 (ES) ................ 200402443

(51) Int. Cl.
*F16F 7/12* (2006.01)
*F16M 13/00* (2006.01)
(52) U.S. Cl. ............................ 188/371; 188/377; 256/1
(58) Field of Classification Search ................. 188/371, 188/373, 377; 256/1, 35, 42; 248/560, 610
See application file for complete search history.

(56) References Cited

U.S. PATENT DOCUMENTS 1,056,576 A * 3/1913 Olson .......................... 256/35
5,207,302 A 5/1993 Popp
5,435,524 A * 7/1995 Ingram ..................... 256/12.5
5,961,099 A * 10/1999 Thommen, Jr. ............ 256/12.5
7,108,233 B2 * 9/2006 Giuseppin ...................... 245/5

FOREIGN PATENT DOCUMENTS

| ES | 2 053 311 | 7/1992 |
|----|-----------|--------|
| ES | 1 028 142 | 12/1994 |
| ES | 1 040 741 | 5/1999 |

* cited by examiner

*Primary Examiner*—Melody M Burch
(74) *Attorney, Agent, or Firm*—Dann, Dorfman, Herrell and Skillman, P.C.; Henry H. Skillman

(57) ABSTRACT

Impact absorbing assembly for slope protection systems, fitted in the containment and protection screens to guard against stones or other bodies landsliding, comprising two cables arranged in the form of loops, each being cased in a "U" shaped tube. The cables are interlaced or arranged in parallel, the loops being fastened together in their upper and lower part by a clamping element compressing the tubes. The cables comprising the invention may be installed taut between the hill anchoring and the protection system, or alternatively, fitted on the mesh support cables with the posts. When an overload occurs on the containment screen, the sudden pull on the cables will force the tubes to become distorted to slide within the clamping elements, the friction leading to a dissipation of energy.

6 Claims, 4 Drawing Sheets

IMPACT ABSORBENT ASSEMBLY IN SLOPE PROTECTION SYSTEMS

CROSS REFERENCE TO RELATED APPLICATIONS

This application is a §365 (c) continuation application of PCT/ES2005/000442 filed Aug. 2, 2005, which in turn claims priority to ES Application No. P200402443 filed Oct. 15, 2004, each of the foregoing applications is incorporated herein by reference.

AIM OF THE INVENTION

This invention, as described in this patent, is an assembly for absorbing impacts in slope protection systems, especially in containment screens and protection against falling stones or other bodies breaking away from hill sides to roll down the slope.

BACKGROUND OF THE INVENTION

When securing land close to roads with traffic and susceptible to the risk of rock landslide, fencing structures are installed using cemented posts in the ground supporting a barrier in the form of a mesh net to contain any falling bodies. These structures incorporate taut anchoring cables between the hill and the fencing.

It has been verified that in the event of considerable elasticity load on this metal mesh, it is insufficient to absorb the kinetic energy, thus leading to breakage of the anchoring cables due to the sudden pull caused by large impacts, another possible effect on the mesh being considerable deformity. In order to equip these structures with a greater dynamic, anchoring cables are installed using loops or lacings with systems that allow for partial deformity of the dimensions of said loop or lacing in the event of substantial loads, thus enabling them to absorb the impact in successive stages.

The European Patent No. 91810923 shows us a loop shaped cable running inside a propeller shaped tube, being compressed on the outside of the ends of the tube by a clamping organ.

In a further European Patent, Utility Model No. 9801738, this cable applies a safety system in landslide zones, by installing cables with tubular loop in the jackstays, made taut between the hill and the post, secured by a slack adjuster at the ends of the loop. These cables, with identical characteristics, are also installed on the upper and lower mesh fastening.

Utility Model 9401490 presents a anti-rock slide screen with a tightening cable with no tubular coating, with loops positioned across clip assemblies operating with brake elements, such that the loop becomes deformed, thus reducing its size as the safety screen is subjected to overload.

SUMMARY OF THE INVENTION

The invention presented here substantially improves on these safety systems outlined above, achieving a balanced dissipation of energy in the event of considerable impacts on the safety mesh. This is achieved with a shock absorbing assembly comprising two cables, each forming a loop with identical dimensions. Each cable is encased in a tube, the loop closed off by securing the cables with a ring.

The loops are located in opposing directions, in their upper and lower parts fitted with clamping elements for a joint fastening at these points, exerting pressure on the tubes while allowing for the tubes to shift when the cables are subject to important overloads on the mesh.

Since the system is fitted with two twin sliding cables, the ability to absorb considerable pulls is greater than in previously known systems, as it distributes the energy evenly in the loops set up in this manner.

DESCRIPTION OF THE DRAWINGS

To complement this description and in order to provide a greater understanding of the characteristics of this invention, this descriptive report is annexed by technical drawings to illustrate the recommended modus operandi, as follows.

DESCRIPTION OF THE PREFERRED EMBODIMENTS

Figure 1:
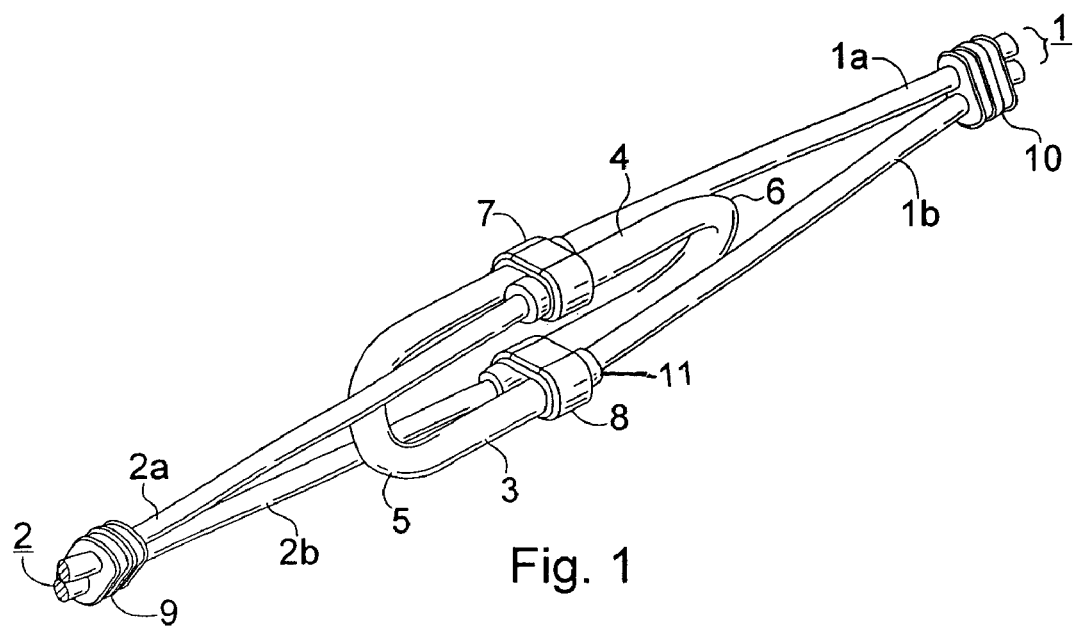
FIG. 1 illustrates cables incorporating an assembly in the recommended manner.
Figure 2:
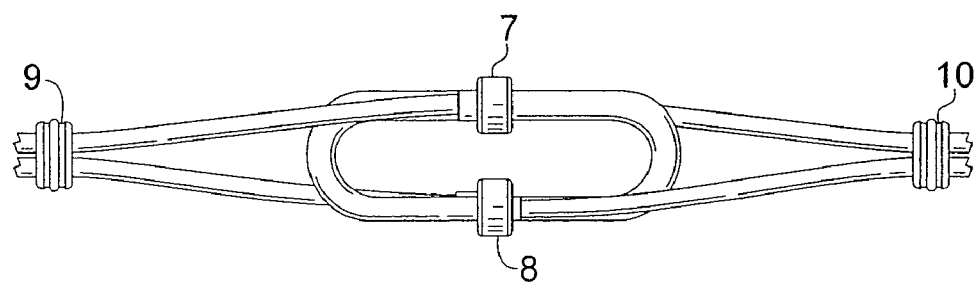
FIG. 2 is a different view of where the cables are positioned.
Figure 3:
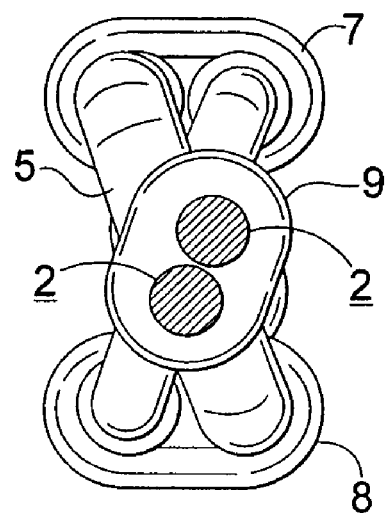
FIG. 3 is a side view of the cables with clamping elements and the retaining ring at the end of the loops.
Figure 4:
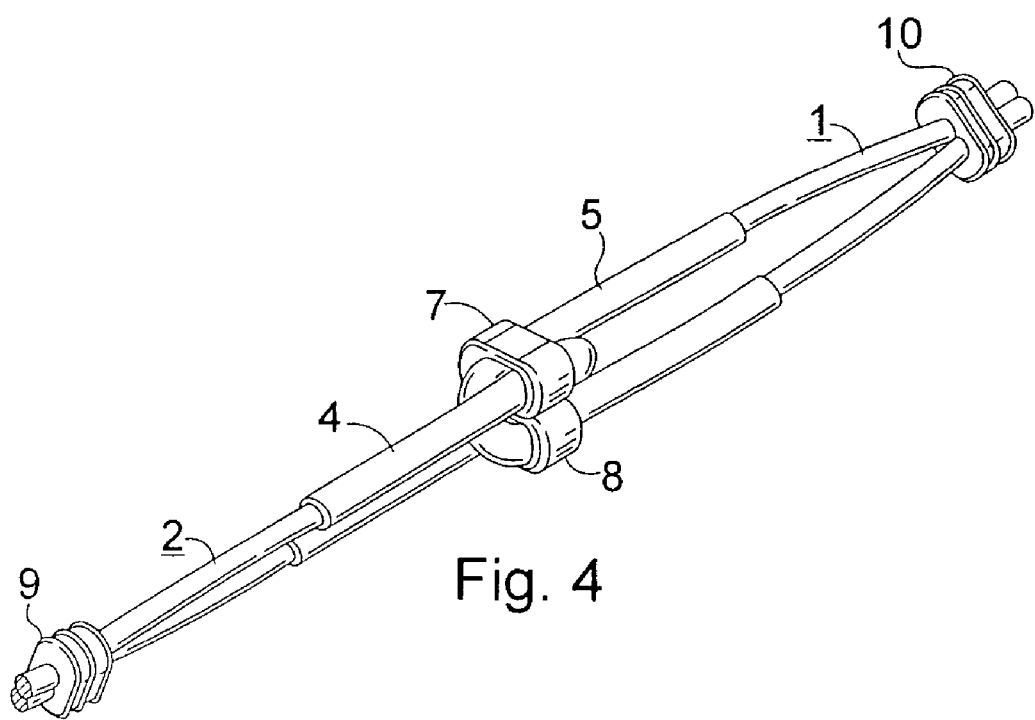
FIG. 4 is a view of the cables installed in the absorbing assembly once the loops are exhausted.
Figure 5:
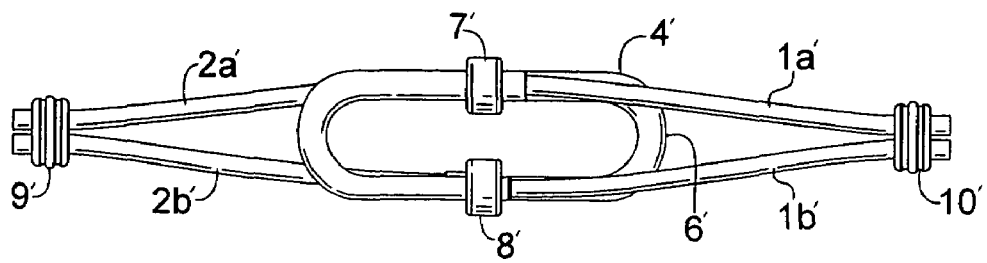
FIG. 5 illustrates cables on the assembly in parallel, in another set-up.
Figure 6:
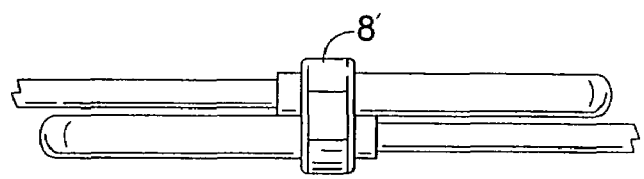
FIG. 6 is another view of the brake cables in parallel.
Figure 7:
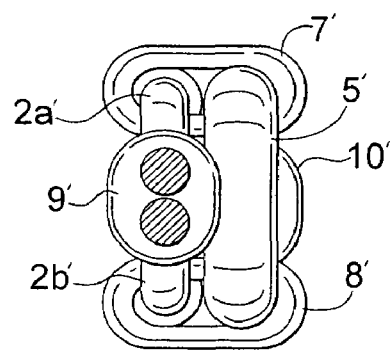
FIG. 7 is a side view of the cables in parallel.
Figure 8:
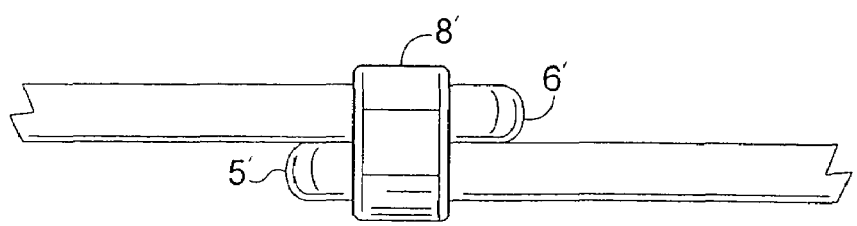
FIG. 8 is a view of the cables in parallel when the loop has been exhausted.

The impact absorbing assembly is adapted to be mounted between the barrier of the slope protection system and anchors in the hill side, or between the barrier and the posts supporting the barrier. The assembly includes two lengths of cable which are interconnected at their ends by forming the ends into loops, preferably by threading the cable through U-shaped tubes, and then interconnecting the loops either in interlocked relation or in parallel relation.

As regards the figures described, the impact absorbing assembly is formed from two identically sized loops formed by cables (1, 2), each cable being cased in a long, narrow "U" shaped tube (3, 4). Each loop has a pair of legs (1a, 1b and 2a, 2b) connected at one end by a curve which is encased in the curve (5,6) in the "U" shaped tube, and at the other end by a ring (9, 10).

Outside the cased part in the "U" shaped tube, the spacing between the legs of the cable loops gradually lessens in size until they meet, the two legs being secured at this point by means of a ring.

Each cable loop set up in this manner is located in the opposite direction to the other. They are located in such a manner that they fasten the two legs to each other in the same position as the two cased tubes (FIGS. 1 to 4). They are secured by clamping elements (7, 8) fitted adjacent the ends of the "U" shaped tubes, applying pressure on the upper and lower legs of the two loops. The clamping elements are to be clamps or pieces that cover the diameter of the cased tubes to distort them in their section, thus reducing their diameter at these points.

It is preferable to secure the two loops in this manner with friction between the tubes (FIGS. 1 to 8).

As the shape of this tube is distorted due to the pressure from the clamping elements, a space is left between the clamping element and the end edge of the tubing in order to avoid the clamping element getting jammed at the edge of the cased tube (11).

The cables are presented as recommended, mutually interlaced (FIGS. 1 to 4), so that the curve on each loop is fitted on the inside perimeter of the other loop. In this set up, when the size of the loops are used up (FIG. 4), the tubes remain jammed at the mid point of the assembly, evenly transferring the shock forces along this point to the rest of the structure.

In an alternative set up, the cables are fitted in parallel and superimposed on top of each other, with no variations in the rest of the invention (FIGS. 5 to 8). Corresponding parts are identified with primed reference characters.

Figure 9:
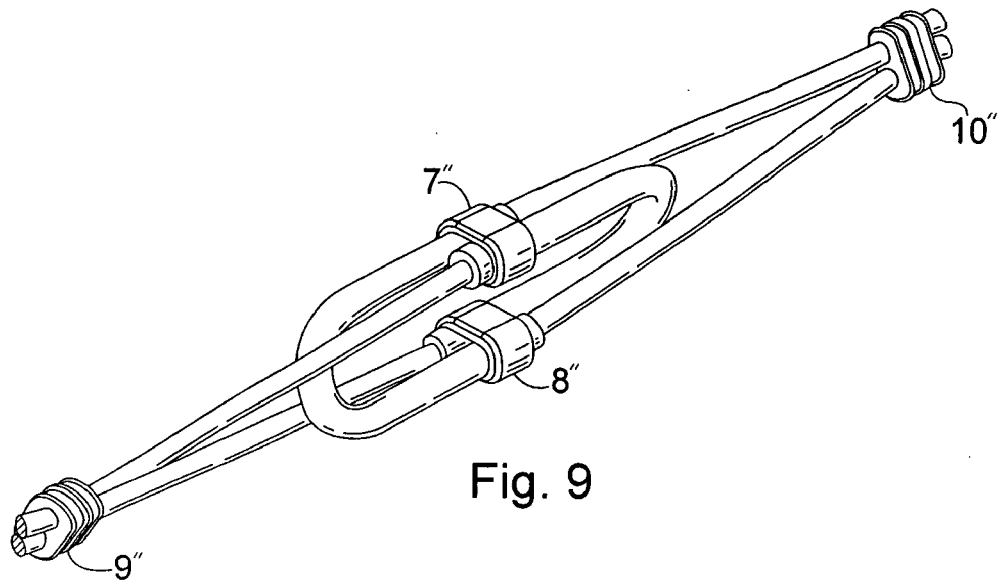
FIGS. 9-12 are views of the assembly in an alternative set up where the clamping elements are configured to avoid any contact between the tubes, both in the interwoven mode and in parallel.
Figure 10:
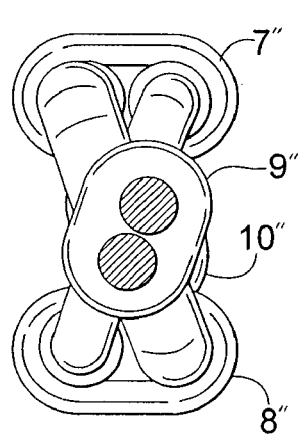
Figure 11:
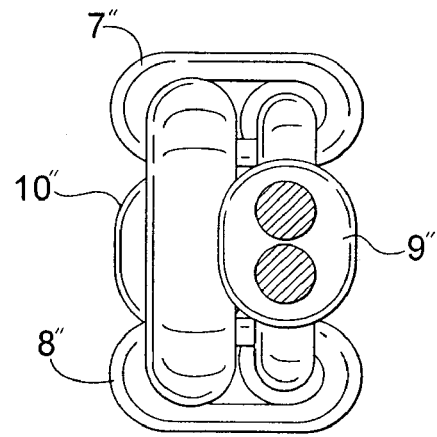
Figure 12:
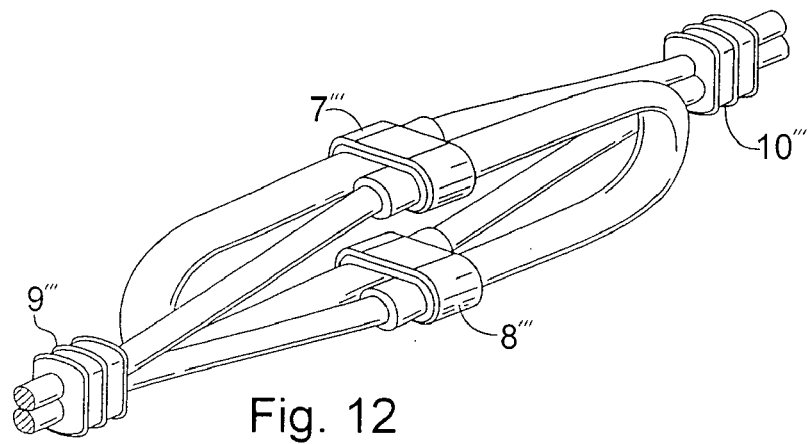

The invention may be modified with clamping elements that allow for a gap between the tubes, either by fastening them in parallel or interlacing them (FIGS. 9 to 12). The assembly in FIGS. 9 and 10 is patterned after the assembly in FIGS. 1-4, and corresponding parts have been identified with corresponding reference characters double primed. The assembly in FIGS. 11 and 12 is patterned after the assembly in FIG. 5-8, and corresponding parts have been identified with corresponding reference characters triple primed.

A further variation (not shown) involves applying bare cables without inserting them into the tubes, in direct contact with the clamping elements.

The set up presented for the invention can be configured on the cables fitted on the safety screen, made taut between the hill anchoring and the protection mesh. Depending on the expected loads that a safety net will have to withstand, support cables for the mesh net may also be installed, between the posts.

In the event that the shock upon the protection mesh from bodies causes an overload on the cables, the shock absorbing assembly will allow for movement of the tubes with cased cable, forcing them to become distorted in section as they pass through the clamping elements cavities, causing energy to be given off due to friction. The length of the assembly is resized until it causes the total exhaustion of the same when the clamping elements reach the curves in the loops (FIG. 4 and 8), at which point the assembly must be replaced.

Depending on the expected loads to be withstood, the materials of the "U" shaped tubes may vary. Likewise, and for the same reasons, the diameters may also be changed. A prediction study will determine the most appropriate clamping elements for each case.

It should be understood that the invention has been described in terms of the recommended set up. Therefore, it may be subject to changes in form, size and materials, on the condition that said alterations involve no substantial variation on the characteristics of the invention as detailed below.

The invention claimed is:

1. Impact absorbing assembly in slope protection systems having a barrier to protect against stones or other bodies breaking away from hillsides, said assembly designed to dissipate the considerable energy loads to which the protection barrier may be subjected, and adapted to be installed taut between a hill anchoring and the protection system, or to be fitted between the barrier and its support posts, said assembly comprising two "U" shaped hollow tubes, each having a pair of legs with open ends and a curve connecting said legs remote from said open ends, two cables forming independent, identical loops, each encased in one of said "U" shaped tubes and having a pair of legs extending out of said open ends of the associated tube and a curve within said curves of the tube, the encased loops being closed at the ends remote from said open ends of said tubes, said cable loops being positioned in opposing directions, and clamping elements located adjacent the open ends of the "U" shaped tubes to fit the two loops together to provide a predetermined length in the assembly between the remote ends of the legs of the cable loops, said clamping elements compressing the tubes, distorting them in their section, whereby in the event of overloads in the protection system, the tubes to are allowed to move longitudinally of said tube legs and said cable legs and resize the said predetermined length.

2. Impact absorbing assembly, according to claim 1, including a ring surrounding said remote ends of each of the cable loops to effect said closure at the remote ends.

3. Impact absorbing assembly, according to claim 1, wherein said tubes are positioned adjoining each other, and said clamping elements exert constrictive pressure on said adjoined tubes.

4. Impact absorbing assembly, according to claim 1, wherein said clamping elements engaging the legs of said two tubes so as to keep the two tubes separate, providing frictional contact between the tubes and the clamping elements, but no frictional contact between one of the tubes and the other of the tubes.

5. Impact absorbing assembly, according to claim 1, wherein said cable loops and tubes are positioned in parallel and superimposed.

6. Impact absorbing assembly, according to claim 1, wherein said cable loops and tubes are interlaced with each other.

* * * * *